US00PP36960P2

(12) United States Plant Patent
Hofmann

(10) Patent No.: US PP36,960 P2
(45) Date of Patent: Sep. 16, 2025

(54) ***Lobularia* PLANT NAMED 'INLBUWHIGT'**

(50) Latin Name: *Lobularia maritima*
Varietal Denomination: INLBUWHIGT

(71) Applicant: Birgit Hofmann, Rudesheim am Rhein (DE)

(72) Inventor: Birgit Hofmann, Rudesheim am Rhein (DE)

(73) Assignee: INNOVAPLANT ZIERPFLANZEN GmbH + Co. KG, Gensingen (DE)

( * ) Notice: Subject to any disclaimer, the term of this patent is extended or adjusted under 35 U.S.C. 154(b) by 0 days.

(21) Appl. No.: 18/956,474

(22) Filed: Nov. 22, 2024

(51) Int. Cl.
*A01H 6/20* (2018.01)
*A01H 5/02* (2018.01)

(52) U.S. Cl.
USPC ..... Plt./263.1

(58) Field of Classification Search
USPC ..... Plt./263.1
CPC ..... A01H 6/20; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lobularia* plant named 'INLBUWHIGT', characterized by its compact, outwardly spreading, mounding to eventually trailing plant habit; freely branching habit; dark green-colored leaves; early and freely flowering habit; long flowering period; relatively large white-colored flowers; tolerance to high temperatures; and good garden performance.

2 Drawing Sheets

Figure 1:
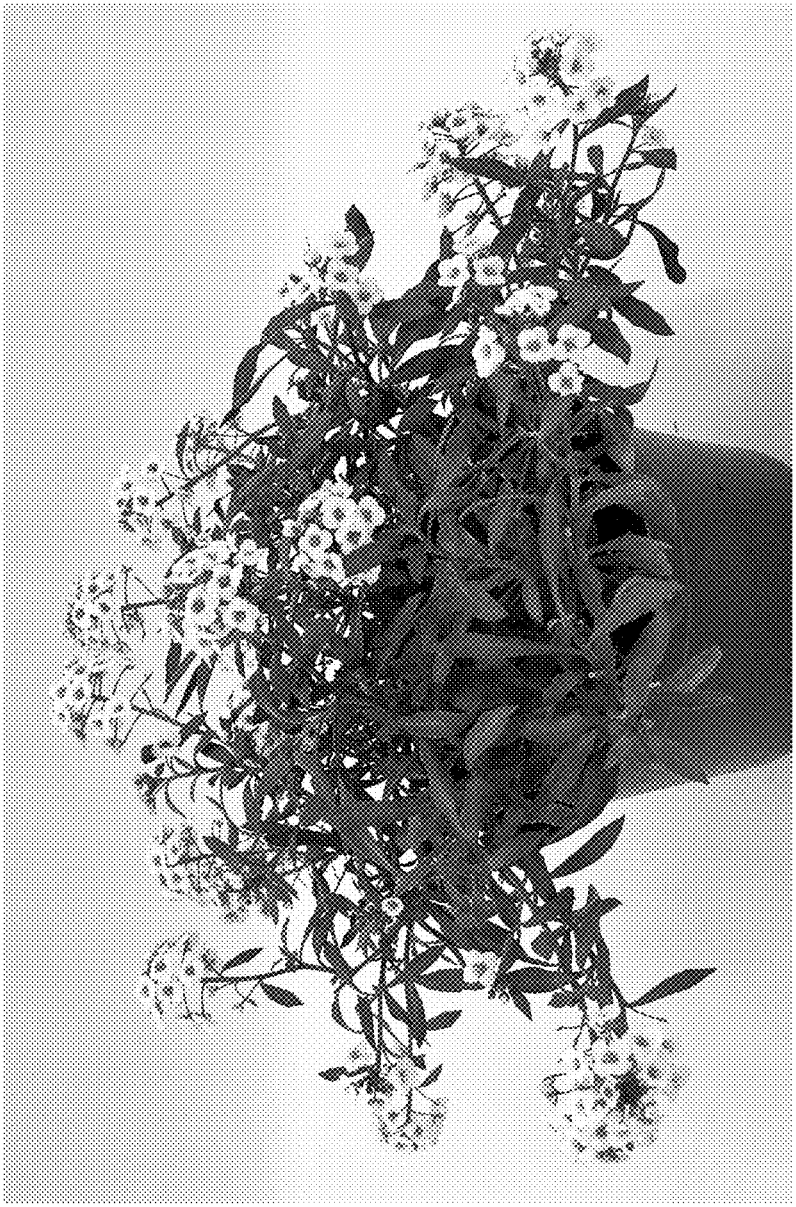

Botanical designation: *Lobularia maritima.*
Cultivar denomination: 'INLBUWHIGT'.

BACKGROUND OF THE INVENTION

The present invention relates to a new and distinct cultivar of *Lobularia* plant, botanically known as *Lobularia maritima*, commonly referred to as Sweet Alyssum and hereinafter referred to by the name 'INLBUWHIGT'.

The new *Lobularia* plant is a product of a planned breeding program conducted by the Inventor in Gensingen, Germany. The objective of the breeding program was to develop new compact and freely-flowering *Lobularia* plants with relatively large flowers and long flowering period.

The new *Lobularia* plant originated from a cross-pollination conducted by the Inventor on Jun. 15, 2020 in Gensingen, Germany of a proprietary selection of *Lobularia maritima* identified as code number lo19-9000-28, not patented, as the female, or seed, parent, with a proprietary selection of *Lobularia maritima* identified as code number lo17-8000-34, not patented, as the male, or pollen, parent. The new *Lobularia* plant was discovered and selected by the Inventor as a single flowering plant within the progeny of the stated cross-pollination in a controlled greenhouse environment in Gensingen, Germany on Sep. 15, 2023.

Asexual reproduction of the new *Lobularia* plant by vegetative terminal cuttings in a controlled greenhouse environment in Gensingen, Germany since Sep. 15, 2023 has shown that the unique features of this new *Lobularia* plant are stable and reproduced true to type in successive generations.

SUMMARY OF THE INVENTION

Plants of the new *Lobularia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INLBUWHIGT'. These characteristics in combination distinguish 'INLBUWHIGT' as a new and distinct *Lobularia* plant:

1. Compact, outwardly spreading, mounding to eventually trailing plant habit.
2. Freely branching habit.
3. Dark green-colored leaves.
4. Early and freely flowering habit.
5. Long flowering period.
6. Relatively large white-colored flowers.
7. Tolerant to high temperatures and good garden performance.

Plants of the new *Lobularia* differ from plants of the female parent selection in the following characteristics:

1. Plants of the new *Lobularia* are not as compact as plants of the female parent selection.
2. Flowers of plants of the new *Lobularia* are larger with larger petals than flowers of plants of the female parent selection.
3. Flowers of plants of the new *Lobularia* are white in color whereas flowers of plants of the female parent selection are dark lilac in color.

Plants of the new *Lobularia* differ from plants of the male parent selection in the following characteristics:

1. Plants of the new *Lobularia* are more compact than plants of the male parent selection.
2. Plants of the new *Lobularia* are more freely branching than plants of the male parent selection.
3. Leaves of plants of the new *Lobularia* are dark green in color whereas leaves of plants of the male parent selection are silvery green in color.

4. Plants of the new *Lobularia* are more freely flowering than plants of the male parent selection.

Plants of the new *Lobularia* can be compared to *Lobularia canariensis* x *Lobularia maritima* 'INLBUSNOPR', disclosed in U.S. Plant Pat. No. 21,594. In side-by-side comparisons, plants of the new *Lobularia* differ from plants of 'INLBUSNOPR' in the following characteristics:

1. Plants of the new *Lobularia* are more compact than plants of 'INLBUSNOPR'.
2. Plants of the new *Lobularia* are more mounding than and not as outwardly spreading as plants of 'INLBUSNOPR'.
3. Leaves of plants of the new *Lobularia* are dark green in color whereas leaves of plants of 'INLBUSNOPR' are greyish green in color.
4. Flowers of plants of the new *Lobularia* are larger with larger petals than flowers of plants of 'INLBUSNOPR'.

BRIEF DESCRIPTION OF THE PHOTOGRAPHS

The accompanying colored photographs illustrate the overall appearance of the new *Lobularia* plant showing the colors as true as it is reasonably possible to obtain in colored reproductions of this type. Colors in the photographs may differ slightly from the color values cited in the detailed botanical description which accurately describe the colors of the new *Lobularia* plant.

The photograph on the first sheet (FIG. 1) is a side perspective view of a typical flowering plant of 'INLBUWHIGT' grown in a container.

Figure 2:
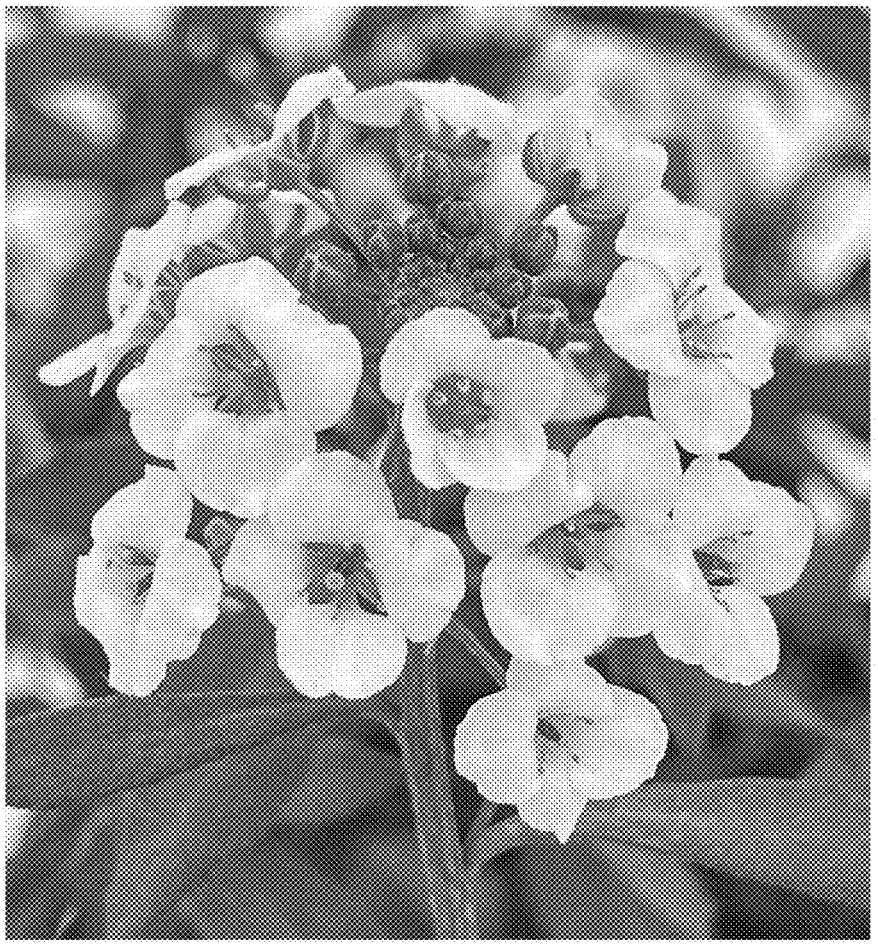

The photograph on the second sheet (FIG. 2) is a close-up view of a typical inflorescence of 'INLBUWHIGT'.

DETAILED BOTANICAL DESCRIPTION

The aforementioned photographs and following observations and measurements describe plants grown during the late summer to early autumn in 813 ml containers in a glass-covered greenhouse in Loudon, New Hampshire and under cultural practices typical of commercial *Lobularia* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Lobularia maritima* 'INLBUWHIGT'.

Parentage:

*Female, or seed, parent*.—Proprietary selection of *Lobularia maritima* identified as code number lo19-9000-28, not patented.

*Male, or pollen, parent*.—Proprietary selection of *Lobularia maritima* identified as code number lo17-8000-34, not patented.

Propagation:

*Type*.—Terminal vegetative cuttings.

*Time to initiate roots, summer*.—About ten days at soil temperatures about 20° C. to 25° C.

*Time to initiate roots, winter*.—About 14 days at soil temperatures about 18° C. to 20° C.

*Time to produce a rooted young plant, summer*.—About 14 days at soil temperatures about 20° C. to 25° C.

*Time to produce a rooted young plant, winter*.—About 20 days at soil temperatures about 18° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Compact, outwardly spreading, mounding and eventually trailing plant habit; freely branching habit with lateral branches potentially developing at every node; dense and bushy appearance; moderately vigorous growth habit and moderate growth rate.

*Plant height*.—About 12 cm to 14 cm.

*Plant diameter* (*area of spread*).—About 32 cm to 36 cm.

*Lateral branches*.—Length: About 16 cm to 18 cm. Diameter: About 1.5 mm to 2.5 mm. Internode length: About 8 mm to 12 mm. Strength: Moderately strong, flexible; wiry. Aspect: Upright to outwardly to eventually trailing. Texture and luster: Moderately to densely pubescent; longitudinally ridged; moderately glossy. Color: Close to 144A.

Leaf description:

*Arrangement*.—Alternate; simple; sessile.

*Length*.—About 3.75 cm to 4 cm.

*Width*.—About 1 cm to 1.25 cm.

*Shape*.—Linear.

*Apex*.—Acute to acuminate.

*Base*.—Cuneate to attenuate.

*Margin*.—Entire, not undulate.

*Texture and luster, upper surface*.—Mostly glabrous with sparse pubescence; slightly glossy.

*Texture and luster, lower surface*.—Smooth, glabrous; slightly glossy.

*Venation pattern*.—Single midvein discernible.

*Color*.—Developing and fully developed leaves, upper surface: Close to 147A; venation, close to 147A. Developing and fully developed leaves, lower surface: Close to 147A to 147B; venation, close to 147A to 147B.

Flower description:

*Flower type and habit*.—Relatively large rotate flowers arranged in axillary and terminal cymes; flowers face initially upright and mostly outwardly with inflorescence development; freely flowering habit, about 25 to 35 flowers per inflorescence.

*Natural flowering season*.—Relatively long flowering period; plants flower continuously from spring until autumn in New Hampshire.

*Flower longevity on the plant*.—Depending on temperatures, flowers last about five to seven days; flowers persistent.

*Fragrance*.—Moderately fragrant; sweet, pleasant.

*Inflorescence height*.—About 3.6 cm to 4.2 cm.

*Inflorescence diameter*.—About 2.2 cm to 2.8 cm.

*Flower diameter*.—About 8 mm to 9 mm.

*Flower depth* (*height*).—About 2.5 mm to 3 mm.

*Flower buds*.—Length: About 2.5 mm. Diameter: About 2 mm. Shape: Roughly spherical to ovoid. Texture and luster: Smooth, glabrous; matte. Color: Developing sepals, close to 144A.

*Petals*.—Quantity and arrangement: Four petals arranged in a single whorl. Lobe length: About 3.5 mm to 4 mm. Lobe width: About 4.5 mm to 5 mm. Shape: Roughly spatulate. Apex: Obtuse. Base: Attenuate with a short stalk; stalk is 1 mm to 1.5 mm in length and 0.5 mm to 1 mm in diameter. Margin: Entire, not undulate. Texture and luster, upper and lower surfaces: Smooth, glabrous; velvety; matte. Color: When opening and fully opened, upper surface: Close to NN155D; venation, close to NN155D; color does not change with subsequent development. When opening and fully opened, lower surface: Close to NN155D; venation, close to NN155D; color does not change with subsequent development.

*Sepals*.—Quantity and arrangement: Four sepals arranged in a single whorl; calyx, cruciform. Length: About 1.5 mm to 2 mm. Width: About 1 mm. Shape: Lanceolate. Apex: Acute to acuminate. Base: Fused at the base. Margin: Entire. Texture and luster, upper surface: Smooth, glabrous; matte. Texture and luster, lower surface: Slightly pubescent; matte. Color, upper and lower surfaces: Close to between 144A and 146A.

*Peduncles*.—Length: About 1 cm to 1.2 cm. Width: About 1 mm. Strength: Moderately strong, wiry and flexible. Aspect: Upright to outwardly. Texture and luster: Smooth, glabrous; longitudinally ridged; slightly glossy. Color: Close to 144A.

*Pedicels*.—Length: About 3.6 mm to 4.2 mm. Width: About 1 mm. Strength: Moderately strong, wiry and flexible. Aspect: Upright to almost horizontal depending on position of the flower on the inflorescence. Texture and luster: Smooth, glabrous; longitudinally ridged; slightly glossy. Color: Close to 144A.

*Reproductive organs*.—Stamens: Quantity per flower: Four. Filament length: About 1.5 mm. Filament color: Close to 144A to 144B. Anther shape: Oblong. Anther size: About 0.5 mm by 1 mm. Anther color: Close to 9A. Pollen amount: None observed. Pistils: Quantity per flower: One. Pistil length: About 2 mm. Style length: About 1.75 mm. Style color: Close to 144A. Stigma shape: Rounded. Stigma color: Close to 144A to 144B. Ovary color: Close to 144A to 144B.

*Seeds and fruits*.—To date, seed and fruit production have not been observed on plants of the new *Lobularia*.

Pathogen & pest resistance: To date, plants of the new *Lobularia* have not been noted to be resistant to pathogens or pests common to *Lobularia* plants.

Garden performance: Plants of the new *Lobularia* have been observed to have good garden performance and to tolerate temperatures ranging from about 4° C. to about 35° C.

It is claimed:

1. A new and distinct *Lobularia* plant named 'INLBUWHIGT' as herein illustrated and described.

* * * * *